US00PP10691P

United States Patent [19]

Vandenberg

[11] Patent Number: Plant 10,691

[45] Date of Patent: Nov. 17, 1998

[54] CHRYSANTHEMUM PLANT NAMED 'BRONZE CANTATA'

[75] Inventor: Cornelis P. Vandenberg, Salinas, Calif.

[73] Assignee: Yoder Brothers, Inc., Barberton, Ohio

[21] Appl. No.: 786,416

[22] Filed: Jan. 21, 1997

[51] Int. Cl.[6] ..... A01H 5/00

[52] U.S. Cl. ..... Plt./82.2

[58] Field of Search ..... Plt./82.2, 82.3

[56] References Cited

U.S. PATENT DOCUMENTS

| | | | |
|---|---|---|---|
| P.P. 8,794 | 6/1994 | Vandenberg | Plt./82.4 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutants in a mutation breeding programme with *Chrysanthemum norifolium*", Euphytica, 29:525–530.

Gosling, ed., 1979, "The Crysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x–rays", Am. Soc. Hort. Sci. Proc., pp. 613–620.

Broertjes, 1966, "Mutation breeding of Chrysanthemums", Euphytica, 15:156–162.

Dowrick et al., 1966, "The induction of mutations in Chrysanthemum using x–and gamma radiation", Euphyrica, 15:204–210.

UPOV–ROM, 1997/04, Plant Variety Database, GTI Jouve Retrieval Software, citation for 'Bronze Cantata'.

*Primary Examiner*—Howard J. Locker

*Attorney, Agent, or Firm*—Foley & Lardner

[57] ABSTRACT

Chrysanthemum plant named 'Bronze Cantata' particularly characterized by its flat capitulum form; daisy capitulum type; light orange-bronze ray floret color; diameter across face of capitulum of 76 to 89 mm when fully opened, when grown as a single stem spray cut mum; flowering response in Salinas under normal temperatures is 48 to 54 days after start of short days. Flowering response in Bogotá, Colombia is 64 to 67 days after start of short days; plant height is 74 to 86 cm when grown in Salinas with 11 long days prior to start of short days; height is 102 to 112 cm when grown in Bogotá with 14 to 15 long days prior to start of short days; peduncle length of the first and the fourth lateral at flowering after removing the apical bud without growth regulator applications is 5 to 15 cm and 8 to 20 cm when grown in Salinas, Calif., and 13 to 20 cm and 20 to 23 cm when grown in Bogotá, Colombia; recommended as a spray cut mum; and uniform flowering in year round flowerings in both Salinas, Calif. and in Bogotá, Colombia.

1 Drawing Sheet

The present invention comprises a new and distinct cultivar of Chrysanthemum, botanically known as *Dendranthema grandiflora,* and referred to by the cultivar name 'Bronze Cantata'.

'Bronze Cantata', identified as 0003 (87-512E07), is a product of a mutation induction program. The new cultivar was discovered and selected by inventor Cornelis P. VandenBerg on Mar. 26, 1993 in a controlled environment in Salinas, Calif. as one flowering plant within a flowering block established as rooted cuttings from stock plants which had been exposed as unrooted cuttings to an X-ray source of 1750 rads in Fort Myers, Fla. on Oct. 8, 1992. The irradiated parent cultivar was the cultivar 'Peach Cantata', disclosed in U.S. Plant Pat. No. 8,794 and described as a flat daisy cut mum with a soft coral-pink ray floret color.

The irradiation program resulting in 'Bronze Cantata' had as its primary objective the expansion of color ranges of the Cantata family and the parent cultivar 'Peach Cantata'. The irradiation program comprised irradiation of cuttings of the parent cultivar at irradiation levels of 1500, 1750 and 2000 rads. A total of 847 cuttings harvested from a total of 225 irradiated plants were planted on Jan. 18, 1993. Of these, 9 initial selections were made, which selections where then revegetated and reflowered. Three consecutive flowerings resulted in discarding 7 of the initial 9 selections on Dec. 6, 1994, and maintaining the remaining two selections as PIs (Possible Introductions), which were further trialed in Salinas, Calif. and in Bogotá, Colombia, ultimately resulting in discarding one remaining selection on Mar. 18, 1995 and the decision to introduce the one remaining selection as 'Bronze Cantata'.

The first act of asexual reproduction of 'Bronze Cantata' was accomplished when vegetative cuttings were taken from the initial selection in May of 1993 in a controlled environment in Salinas, Calif., by technicians working under supervision of Cornelis P. VandenBerg.

Horticultural examination of controlled flowerings of successive plantings has shown that the unique combination of characteristics as herein disclosed for 'Bronze Cantata' are firmly fixed and are retained through successive generations of asexual reproduction.

'Bronze Cantata' has not been observed under all possible environmental conditions. The phenotype may vary significantly with variations in environment such as temperature, light intensity and daylength, without, however, any variance in genotype.

The following observations, measurements and comparisions describe plants grown in Salinas, Calif., and in Bogotá, Colombia, under greenhouse conditions which approximate those generally used in commercial greenhouse practice. The low night temperature tolerance was determined in repeated flowerings in Bogotá, Columbia, with an average minimum low night temperature inside the greenhouse during our trials ranging as low as 5 to 8 degrees Celsius.

The following traits have been repeatedly observed and are determined to be basic characteristics of 'Bronze Cantata', which, in combination, distinguish this Chrysanthemum as a new and distinct cutlivar:

1. Flat capitulum form.
2. Daisy Capitulum type.
3. Light orange-bronze ray floret color.

4. Diameter across face of capitulum of 76 to 89 mm when fully opened, when grown as a single stem spray cut mum.

5. Flowering response in Salinas under normal temperatures is 48 to 54 days after start of short days. Flowering response in Bogotá, Columbia is 64 to 67 days after start of short days.

6. Plant height is 74 to 86 cm when grown in Salinas with 11 long days prior to start of short days; height is 102 to 112 cm when grown in Bogotá with 14 to 15 long days prior to start of short days.

7. Peduncle length of the first and the fourth lateral at flowering after removing the apical bud without growth regulator applications is 5 to 15 cm and 8 to 20 cm when grown in Salinas, Calif., and 13 to 20 cm and 20 to 23 cm when grown in Bogotá, Columbia.

8. Recommended as a spray cut mum.

9. Uniform flowering in year round flowerings in both Salinas, Calif. and in Bogotá, Columbia.

10. Excellent low night temperature tolerance, flowering in Bogotá, Colombia at average minimum low night temperatures inside the greenhouse as low as 5° to 8° C.

The accompanying photographic drawing is a side view of a single stem cut spray mum of 'Bronze Cantata', with the colors being as nearly true as possible with illustrations of this type.

Of the commercial cultivars known to the inventor, the most similar in comparision to 'Bronze Cantata' is the parent cultivar 'Peach Cantata' (U.S. Plant Pat. No. 8,794). All traits of 'Bronze Cantata' are similar to those of 'Peach Cantata', except for the ray floret color. The ray floret color of 'Bronze Cantata' is light orange-bronze (R.H.S. 16A), while the ray floret color of 'Peach Cantata' is described as soft coral-pink (R.H.S. 36C to 36D).

Chart A compares certain characteristics of 'Bronze Cantata' to those same characteristics of 'Peach Cantata', 'White Cantata' (U.S. Plant Pat. No. 8,795), and 'Lemon Cantata' (U.S. Plant Pat. No. 8,796).

CHART A

| Characteristic | Bronze Cantata | Peach Cantata | White Cantata | Lemon Cantata |
|---|---|---|---|---|
| Capitulum face diameter | 76–89 mm | 76–89 mm | 76–89 mm | 72–89 mm |
| Flower color (RHS): | | | | |
| Upper surface: | 16A | 36C–36D | 155D | 10D–11D |
| Lower surface: | 16C | 36D | 155D | 10D–11D |
| Plant height (with long days prior to start of short days) | 74–86 cm(11 days in Salinas); 102–112 cm (14–15 days in Bogota) | 61–86 cm(11 days in Salinas); 102–112 cm (14–15 days in Bogota) | 76–91 cm(11 days in Salinas); 99–109 cm (14–15 days in Bogota) | 71–91 cm (3–11 days in Salinas); 99–107 cm (14–15 days in Bogota) |

In general comparison, the main difference among the cultivars is ray floret color, with only slight differences occurring in size.

In the following description color references are made to The Royal Horticultural Society Colour Chart. The color values were determined on plant material grown as a single stem spray cut mum grown in Salinas, Calif. on Jun. 3, 1996.

Classification:

*Botanical.*—*Dendranthema grandiflora* cv 'Bronze Cantata'.

*Commercial.*—Flat daisy spray cut mum.

Inflorescence

A. Capitulum:

*Form.*—Flat.

*Type.*—Daisy.

*Diameter across face.*—76 to 89 mm when fully opened.

B. Corolla of ray florets:

*Color* (*general totally from a distance of three meters*) .—Light orange-bronze.

*Color* (*upper surface*).—16A.

*Color* (*under surface*).—16C.

*Shape.*—Straight, oblong, slightly ribbed.

C. Corolla of disc florets:

*Color* (*mature*).—Closest to 14A to 14B.

*Color* (*immature*).—Closest to 144B.

D. Reproductive organs:

*Androecium.*—Present on disc florets only; moderate pollen.

*Gynoecium.*—Present on both ray and disc florets.

Plant

A. General appearance:

*Height.*—74 to 86 cm when grown in Salinas with 11 long days prior to start of short days; height is 102 to 112 cm when grown in Bogotá with 14 to 15 long days prior to start of short days.

B. Foliage:

*Color* (*upper surface*).—147A.

*Color* (*under surface*).—147B.

*Shape.*—Deeply lobed and serrated.

What is claimed is:

1. A new and distinct Chrysanthemum plant named 'Bronze Cantata', as described and illustrated.

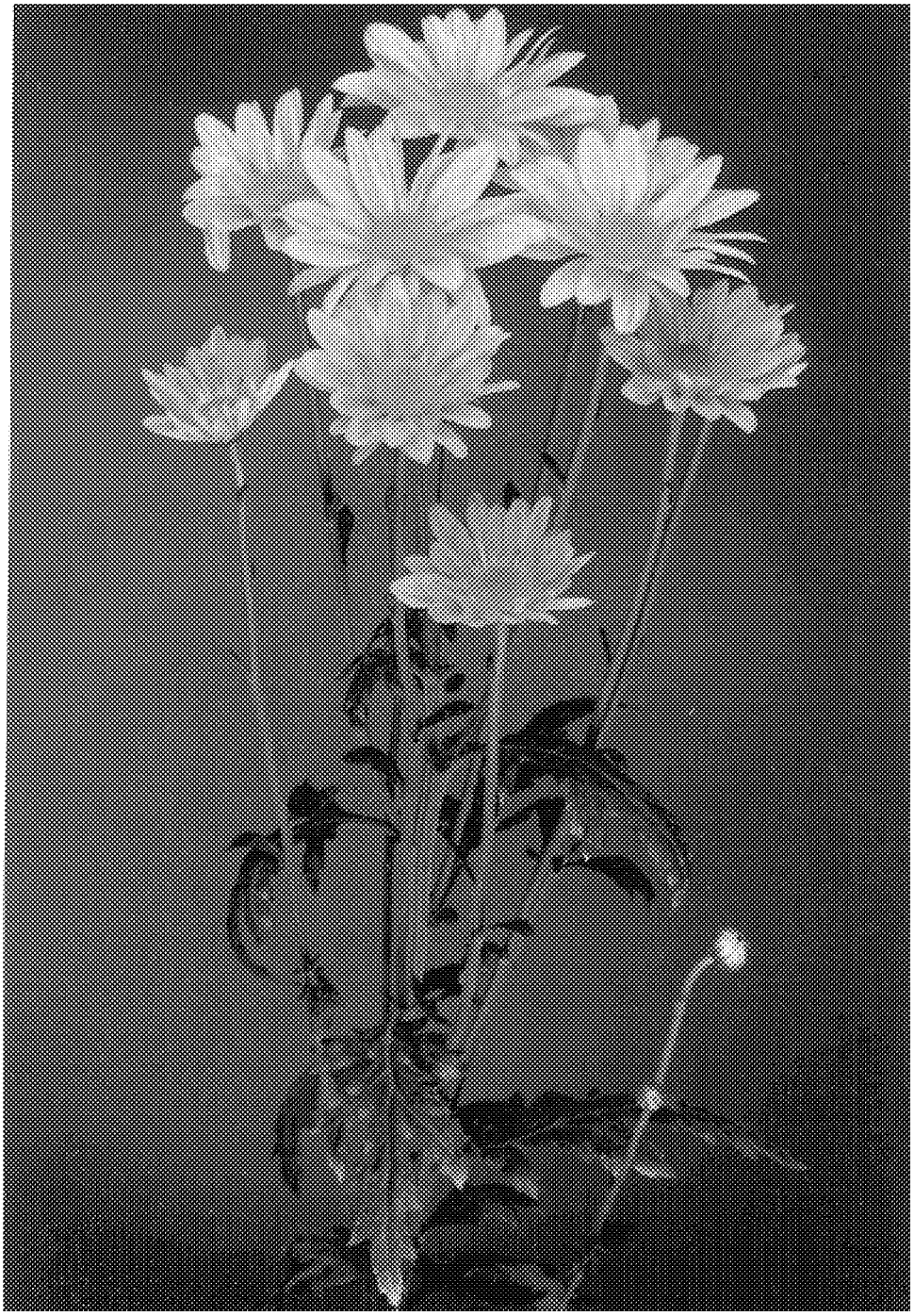

* * * * *